(12) United States Patent
Williams et al.

(10) Patent No.: US 9,951,037 B2
(45) Date of Patent: Apr. 24, 2018

(54) PROCESS FOR THE PREPARATION OF 4-PHENYLDIBENZOTHIOPHENE

(71) Applicant: Albemarle Corporation, Baton Rouge, LA (US)

(72) Inventors: Eric L. Williams, Zachary, LA (US); Dean K. Hoglen, Baton Rouge, LA (US)

(73) Assignee: ALBEMARLE CORPORATION, Baton Rouge, LA (US)

( * ) Notice: Subject to any disclaimer, the term of this patent is extended or adjusted under 35 U.S.C. 154(b) by 0 days.

(21) Appl. No.: 15/525,492

(22) PCT Filed: Dec. 1, 2015

(86) PCT No.: PCT/US2015/063237
§ 371 (c)(1),
(2) Date: May 9, 2017

(87) PCT Pub. No.: WO2016/094135
PCT Pub. Date: Jun. 16, 2016

(65) Prior Publication Data
US 2018/0022725 A1     Jan. 25, 2018

Related U.S. Application Data

(60) Provisional application No. 62/091,119, filed on Dec. 12, 2014.

(51) Int. Cl.
*C07D 333/76*     (2006.01)
(52) U.S. Cl.
CPC .................. *C07D 333/76* (2013.01)
(58) Field of Classification Search
CPC .................................. C07D 333/76
USPC ........................................... 549/43
See application file for complete search history.

(56) References Cited

U.S. PATENT DOCUMENTS

2013/0069049 A1    1/2013   Park et al.
2014/0001442 A1    1/2014   Lee et al.

FOREIGN PATENT DOCUMENTS

WO     2013/012296 A1    1/2013

OTHER PUBLICATIONS

Gilman, Henry, et al., "Dibenzothiophene: Orientation and Derivatives", Journal of Organic Chemistry, vol. 3, May 1938, pp. 108-119.
McCall, E. B., et al., "Derivatives of Dibenzofuran and Dibenzothiophen. Part II. Free-radical Phenylation of Dibenzothiophen", Journal of Organic Chemistry, 1962, pp. 5288-5290.
Ruhlandt-Senge, et al., "The synthesis and characterization of metal derivatives of the new, conveniently prepared, bulky thiolato ligand HSC6H2-2,4,6-Ph3", Bull. Soc Chim Fr, 1992, vol. 129, 594-598.
Saednya, Akbar, et al., "Two Efficient Routes to m-Terphenyls from 1,3-Dichlorobenzenes", Synthesis, 1996, pp. 1455-1458.
Murata, Shizuaki, et al., "Syntheses of Dibenzo[c,e]]1,2]diselenin and Related Novel Chalcoginide Heterocyclic Compounds", Journal of Heterocyclic Chemistry, 1991, pp. 433-438.

*Primary Examiner* — Taofiq A Solola
(74) *Attorney, Agent, or Firm* — Marcy M. Hoefling

(57) ABSTRACT

The invention relates to a novel method for the preparation of 4-phenyldibenzo[b,d]thiophene which can be conducted in one pot up to the thiophene ring formation. The synthesis is based upon dihalobenzenes and phenyllithium, which are readily obtainable, and can give higher yields (based upon either reactant) than the yields current methods, which use a synthetic pathway based upon dibenzo[b,d]thiophene.

10 Claims, No Drawings

PROCESS FOR THE PREPARATION OF 4-PHENYLDIBENZOTHIOPHENE

CROSS-REFERENCE TO RELATED APPLICATIONS

This application is the National Stage of International Application No. PCT/US2015/063237, filed on Dec. 1, 2015, which claims the benefit of U.S. Provisional Application No. 62/091,119, filed Dec. 12, 2014. Each patent application identified above is incorporated here by reference in its entirety.

TECHNICAL FIELD

The invention relates to a novel method for the preparation of 4-phenyldibenzo[b,d]thiophene.

BACKGROUND

The compound 4-phenyldibenzo[b,d]thiophene is in demand for use as a host component in Organic Light Emitting Diodes (OLEDs). The compound has heretofore been synthesized according to a process which involves the metallation of dibenzo[b,d]thiophene with n-butyllithium. The resulting 4-lithiodibenzo[b,d]thiophene is reacted with trimethylborate, followed by hydrolysis with acid to give 4-dibenzo[b,d]thiophene boronic acid. The boronic acid is then reacted with bromobenzene under palladium catalyzed Suzuki conditions to give 4-phenyldibenzo[b,d]thiophene. The foregoing synthetic strategy is not conveniently a "one pot" synthetic scheme: it is generally prepared in several separate steps, with product transfers and purifications associated with each step, each of which significantly decreases yield. Furthermore, the synthesis uses dibenzo[b,d]thiophene as a precursor. Dibenzo[b,d]thiophene is expensive because it is a multi-ring heterocycle, which costs more to synthesize than other, less structurally complex starting materials. Syntheses used here-to-fore are thus economically inefficient in that they are relatively low-yielding with respect to dibenzo[b,d]thiophene, an expensive reactant used in the first synthetic step.

SUMMARY OF THE INVENTION

Applicant has discovered a synthesis of terphenyl thiophenes of the following general structure:

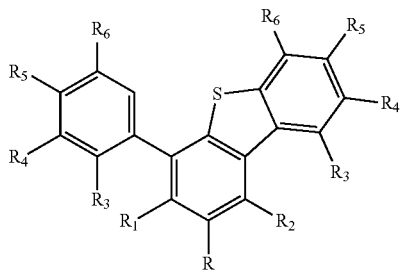

In one aspect of the invention the synthesis gives a product in which all R substituents are hydrogen, and the product is 4-phenyldibenzo[b,d]thiophene:

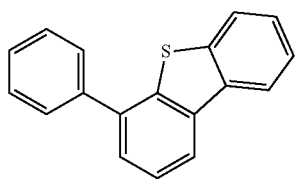 [SMILES: c1ccc(-c2cccc3c2sc2ccccc23)cc1]

The method comprises the steps of reacting a dihalobenzene with phenyllithium to give a terphenyllithium:

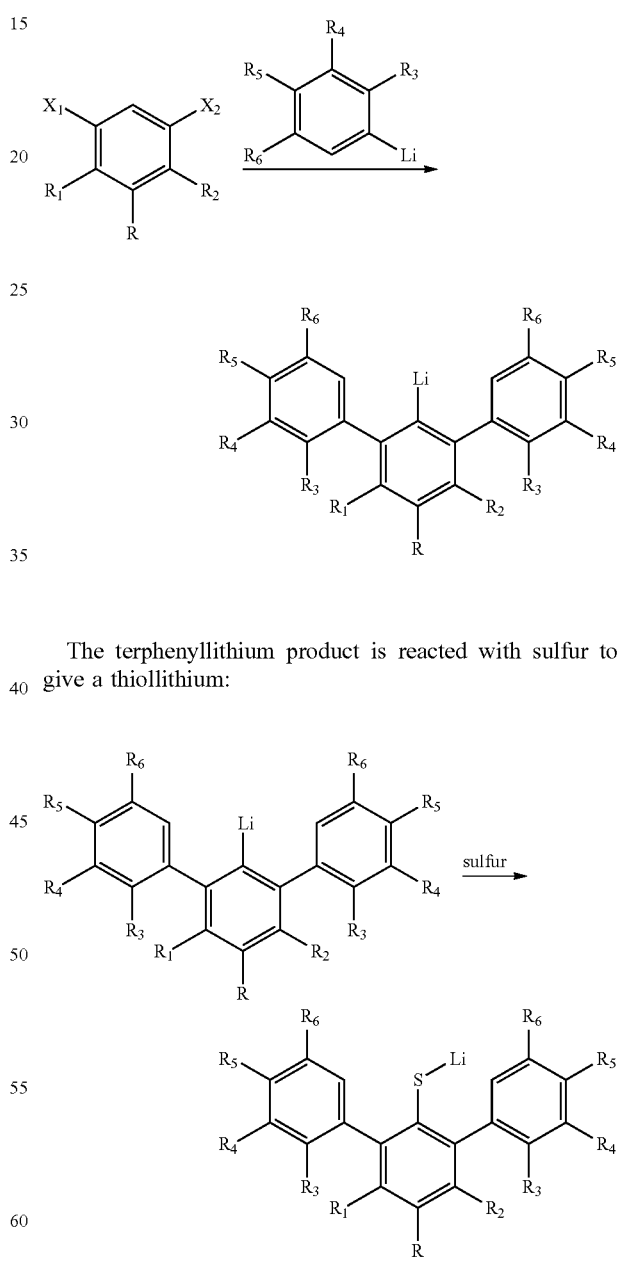

The terphenyllithium product is reacted with sulfur to give a thiollithium:

A thiol is formed by treatment of the thiollithium with acid. The thiol is further reacted in the presence of an oxidizer, which, in some embodiments, is sulfur, to give the 4-phenyldibenzo[b,d]thiophene:

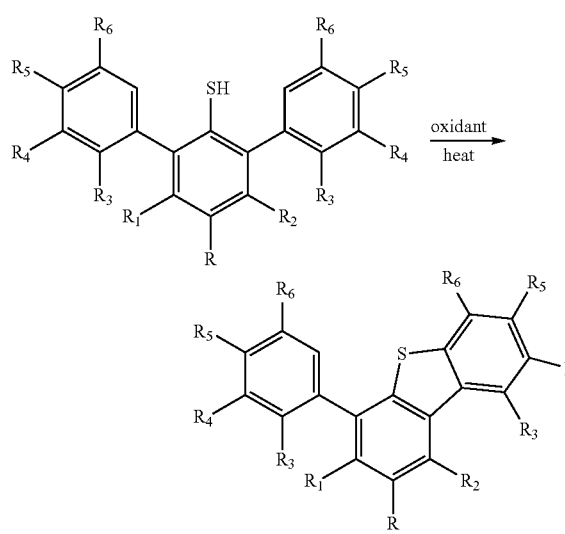

For purposes of these formulas, R, $R_1$, $R_2$, $R_3$, $R_4$, $R_5$, and $R_6$ are each independently selected from the group consisting of hydrogen, phenyl, an alkyl substituent (—$C_n$) and an ether substituent (—$C_{m1}$—O—$C_{m2}$), where n, m1 and m2 are each an integer, with each of n and (m1+m2+1) being in the range of 0 to 16; and $X_1$ and $X_2$ are each independently selected from the group consisting of chlorine, iodine and bromine.

The above method for the preparation of 4-phenyldibenzo[b,d]thiophene is generally carried out using four synthetic components, dihalobenzene, phenyllithium, sulfur and an oxidant. In the case in which where sulfur is used as an oxidant, only three different, relatively inexpensive, easily obtained synthetic components are required. The above synthesis can be conducted as substantially a "one pot" synthesis, which minimizes purification, solvent changes and transfers which negatively impact yield. In one aspect of the invention, the phenyllithium is prepared as a prestep to the synthetic process given above, which can be used in "one pot" continuity with the synthesis. Based upon the current market prices of the reactants and reagents, as well as the cost of other incidentals, such as heating energy, which are necessary to synthesize 4-phenyldibenzo[b,d]thiophene by the method disclosed herein, it is expected that the target compound can be manufactured for less than about a quarter of its present market price.

These and other embodiments and features of this invention will be still further apparent from the ensuing description and appended claims.

FURTHER DETAILED DESCRIPTION OF THE INVENTION

The synthesis comprises the step of contacting phenyllithium and a dihalobenzene in the presence of a solvent and under conditions sufficient to give a terphenyllithium. The phenyllithium can be prepared by methods known in the art, such as, for example, the reaction of lithium metal and bromobenzene in solvent such as ether. The phenyllithium can be substituted, but at least one of the ring positions adjacent the lithium-substituted carbon should be unsubstituted. The substituents, corresponding to $R_3$, $R_4$, $R_5$ and $R_6$, each are independently selected from the group consisting of hydrogen, phenyl, alkyl substituents (—$C_n$) or ether substituents (—$C_{m1}$—O—$C_{m2}$), where n, m1 and m2 are integral, with n and (m1+m2+1) being in the range of 1 to about 16, or, in other aspects, in a range of about 1 to about 6. It is preferred that the phenyllithium be formed under an inert atmosphere, such as, for example, helium, argon, nitrogen, or the like. In some aspects, the solvent is one or more ethers, such as, for example, diethyl ether, dibutyl ether, and the like.

In general, the formation of phenyllithium from lithium and bromobenzene can be a time-consuming reaction. One reaction method involves the addition of lithium metal to a reaction vessel containing solvent, followed by the measured addition of bromobenzene over an extended period of time, such as in the range of about 2 to about 6 hours. A reaction time in the range of from about 2 to about 4 hours can be expected at temperatures in the range of about 20 to about 35° C. In general, if one pot synthesis is desired, the solvent is preferably inert to reaction with reactants and products of the remaining steps of the synthesis which require solvent (phenyllithium formation, terphenyl formation, thiollithium formation, thiol formation) and able to solvate them. For example, suitable solvents include those which are not easily converted to disulfides or thiophenols during the terphenyl thiol formation step. Thus, suitable solvents generally include, for example, ethers and alkanes. Preferred solvents include diethyl ether, dibutyl ether, pentane, hexane, heptane and the like. If desired, the reaction mixture can be stirred during the reaction. In general, because of the propensity of Lithium to react with dichlorobenzene, a reactant, it is strongly preferred that the formation of the phenyllithium proceed to substantial completion before the terphenyl-forming reaction.

The synthesis further comprises the contacting of phenyllithium with a dihalobenzene. The dihalobenzene comprises two halogen substituents, X1 and X2, in a meta-substitution arrangement (i.e., a m-dihalobenzene), with one halogen on each side of an unsubstituted benzene carbon. In some aspects of the invention, the halogen atoms are such that $X_1$ and $X_2$ are each independently selected from the group consisting of chlorine, iodine and bromine. In more preferred aspects, $X_1$ and $X_2$ are each chlorine; $X_1$ is chlorine and $X_2$ is iodine; $X_1$ is chlorine and $X_2$ is bromine; or $X_1$ and $X_2$ are each bromine.

The dihalobenzene can be substituted at one or more of the three remaining ring positions. The substituents, corresponding to R, R1 and R2, are each independently selected from the group consisting of phenyl, hydrogen, alkyl substituents (—$C_n$) or ether substituents (—$C_{m1}$—O—$C_{m2}$), with n and (m1+m2+1) being in the range of 1 to about 16, or, in another embodiment, in the range of about 0 to about 6.

In one aspect of the invention, the reaction of the phenyllithium with the dihalobenzene takes place sequentially in the same flask, container, or pot and in the same solvent or reaction mixture in which the phenyllithium was formed ("one pot"). In further aspects, the steps sequentially take place in the same solvent. It is strongly preferred to maintain an inert atmosphere during the reaction of phenyllithium with dihalobenzene.

The terphenyl-formation reaction temperature is not critical, and in general, the reaction can be conducted at one or more of a wide range of temperatures. Because the reaction is exothermic, it can be useful to employ a cooling means, such as, for example, a cooling jacket. In some aspects the temperature is maintained, with the aid of a cooling means, if necessary, at one or more temperatures in the range of from about 0° C. to about 100° C. In other narrower aspects, the temperature is maintained at one or more temperatures between about 15° C. and about 30° C.

In general, the terphenyl-formation reaction is formed by contacting the phenyllithium and dihalobenzene in a solvent. In one aspect of the invention, the reaction is performed by the addition of dihalobenzene to the reaction vessel containing the phenyllithium and solvent. The addition can be performed all at once, or incrementally, such as by dropwise addition. If dropwise, the addition can take place over a period of time, such as in the range of about 1 to about 3 hours. If the contacting is done all at once, at a temperature in the range of 0° C. to about 100° C., the formation of the terphenyllithium takes place over a time period of about 1 to about 2 hours and is preferably with agitation over at least some of the formation time. If the contacting is performed incrementally, such as dropwise, over longer periods, the reaction time can be given by the rate of addition of the added component.

In general, the mechanism of the process requires three phenyllithium molecules per dihalobenzene in order to give a terphenyllithium. The phenyl groups of two of the three phenyl groups become part of the terphenyl molecule. The third required phenyllithium gives rise to an aryl byproduct, which in the case of unsubstituted phenyllithium, is benzene. In order to have a complete reaction, the molar ratio of phenyllithium to added dihalobenzene should be at least three. In one aspect of the invention, the foregoing ratio is in the range of about 3 to about 5. An amount of phenyllithium of three equivalents or greater is required for complete conversion of all dichlorobenzene. However, in order to maximize conversion, a stoichiometric excess of phenyllithium is generally used.

The thiollithium is formed by reacting the terphenyllithium with sulfur. The reaction is exothermic. In general, it is preferred to cool the reaction mixture to remove some of the heat generated by the reaction. The reaction can be conducted in the same reaction vessel as the terphenyl-formation step. If so, it is preferable to cool the reaction mixture to a temperature in the range of about 0 to about 5° C. prior to the addition of the sulfur. The sulfur can be added all at once or incrementally, such as in portions over time, such as over a time in the range of about 1 to about 2 hours. In one aspect, the temperature is maintained within the range of about 0 to about 15° C. during the addition of the sulfur. In another aspect, the temperature is maintained within the range of about 0 to about 15° C. during the addition of the sulfur. The reaction mass is preferably vigorously stirred during the sulfur addition.

It is preferred to add the sulfur over time at such a rate as to keep the concentration of unreacted sulfur low enough to minimize the formation of impurities. In one aspect of the invention, the mole ratio of excess (unreacted) sulfur to thiollithium at any time during the addition of the sulfur is in the range of from about 0 to about 3. In further aspects, the mole ratio of unreacted sulfur to thiollithium is in the range of about 0 to about 1. After sulfur addition, the reaction can be agitated for a time prior to the thiol formation reaction, but the thiollithium formation is generally complete at the end of the sulfur addition.

The subsequent thiol formation preferably takes place at temperatures maintained between about 10 and about 45° C., and in narrower aspects, between about 10 and about 30° C. In one aspect, the reaction mass is warmed to a temperature between about 10 and about 30° C. as soon as the addition is complete.

The thiol is formed by the addition of an acid. The acid is added as an aqueous solution and, in the absence of agitation, an aqueous, acid-containing layer forms which is separable from the remainder of the reaction mixture. The reaction is heterogeneous, and thus agitation of the reaction mass during the addition of the acid is preferred. The acid can be added all at once, or dropwise over a period of time. In some aspects of the invention, the acid is added dropwise, over a time period in the range of about 1 to about 3 hours. In some aspects of the invention, the acid is added at one or more temperatures in the range of about 5 to about 50° C., or in other aspects in the range of about 10 to about 30° C. While a range of different protic acids can be used, one or more of hydrochloric acid, hydrobromic acid, sulfuric acid, and acetic acid are preferred.

Theoretically, in order to essentially fully protonate the thiol, enough acid must be added such that at least an equivalent of protons is provided with respect to the thiol. However, the amount of acid added to the reaction mixture can depend upon the amount of phenyllithium remaining in the reaction mixture. As mentioned above, stoichiometrically, the formation of the terphenyllithium theoretically requires the use of three equivalents of phenyllithium per equivalent of dihalobenzene. Two equivalents of phenyllithium are fated to become part of the terphenyl backbone, while one equivalent becomes a benzene (or substituted benzene) byproduct. It has been found that approximately about 3.5 to 7, and more preferably 4.5 to 5.5 equivalents of phenyllithium per equivalent of dihalobenzene will improve the yield of terphenyllithium. In such cases, the terphenyllithium can be present in stoichiometric excess with respect to the amount needed to fully convert the dihalobenzene to terphenyllithium. Enough acid should be added to protonate the excess terphenyllithium, as well as protonate the thiollithium to give the thiol.

In general, the molarity of the acid solution is in the range of about 2 to about 3 moles per liter of water. It is preferred that the acid be added such that the molar amount added is in the range of about 3% to about 5% percent of molar excess of the molar amount of thiollithium combined with the molar amount of excess phenyllithium.

After thiol formation, acid is separated from the reaction mass, preferably by removal of the aqueous layer which contains the acid. In one aspect of the invention, this layer can be drained away from the reaction mass.

In one aspect, the above synthesis steps are carried out in one pot. There is no need to change or remove solvent. The thiol is then separated out of the reaction mixture, which also comprises the solvent. Generally, the reaction mixture will contain thiophenol compounds and possibly other sulfur-bearing aromatic compounds formed by the sulfidation of residual prior step reactants, including sulfides such as, for example diphenyl disulfide, as well as any thiophenol formed in the thiol formation reaction. The separation can generally be accomplished by distillation. In order to further reduce the amount of thiophenol and disulfide impurities, the solid product can be filtered through a fine mechanical separating means such as, for example, diatomaceous filtration aids, such as those manufactured under the brand name Celite™. The filter material can be washed with fresh portions of solvent. The solid product can be washed from the filtration material with solvent into a flask and again subjected to distillation. In general the distillations are conducted at one or more temperatures in the range of about 30 to about 180° C., and at pressures in the range of about 300 to about 2 Torr. More preferred are distillation temperatures in the range of about 30 to about 130° C., and pressures in the range of about 100 to about 8 Torr. It is thus preferred to use one or more solvents which have boiling points in the foregoing temperature and pressure ranges.

Solvents which can be used in the further distillation include diethyl ether, dibutyl ether, pentane, hexane, heptane. In one aspect, the solvent used to further distill the thiol is the same solvent in which the thiol was prepared. In further aspects, the solvent for both synthesis of the thiol and purification of the thiol is diethylether or dibutyl ether.

The dibenzothiophene is prepared from the thiol by contacting the thiol with an oxidizing agent to form a dibenzothiophene ring involving the thiol group and one of the laterally placed phenyl rings. The reaction is conveniently conducted under an inert atmosphere, which, although not essential, provides effective control over the conditions of oxidation. Examples of inert atmospheres include nitrogen or argon. In preferred aspects of the invention, the oxidizing agent comprises sulfur atoms, and in further aspects, the oxidizing agent is one or more of elemental sulfur, sulfuryl chloride, chlorine, and bromine and the like. In one a preferred aspect of the invention, the oxidizing agent is elemental sulfur. The reaction between the oxidizing agent and the thiol can be performed neat (i.e., in the absence of solvent). However, in the case of sulfuryl chloride, it is preferred to use a solvent, such as, for example, isohexane, heptane, and other alkanes. Other solvents that are inert to the sulfuryl chloride can be used.

It has been found that trace amounts of amines, such as, for example, triethylamine can serve as a catalyst or initiator. Such initiators can be included in amounts in the range of about 0.001 to about 0.1 mol equivalents wt %, and more preferably in the range of about 0.0014 to about 0.002 mol equivalents wt %, based upon the weight of the thiol. The exact amounts have been found not to be critical. The oxidizing agent can be combined with the thiol in a reaction vessel. Any volatiles, such as, for example, any liquids used in the transfer of the thiol or oxidizing agent, can be distilled off or otherwise removed. The thiol and the oxidizing agent are heated. In some aspects of the invention, the contents of the reaction vessel are heated to one or more temperatures in the range of about 180 to about 250° C. In further aspects, the temperature is in the range of about 230 to about 235° C. It is preferred that the temperature be raised over a time period in the range of about 1 to about 4 hours. In a preferred aspect, the oxidizing agent comprises one or more of elemental sulfur and sulfuryl chloride, and the reaction vessel is heated to one or more temperatures in the range of about 230 to about 235° C., with the heating to the foregoing temperatures taking place over a time in the range of about 1 to about 2 hours.

When sulfuryl chloride is used as the oxidizing agent, an advantage is that the reaction can be run at relatively low temperatures. However, the sulfuryl chloride essentially gives a chlorinated sulfur group which must be further subjected to a ring closure reaction. A Friedel-Crafts ring closure can be effected through the further use of aluminum chloride.

The method of the present invention provides a synthesis for the preparation of a wide variety of substituted 4-phenyldibenzo[b,d]thiophenes. It is not unusual with the present method to obtain a product yield, based upon dichlorobenzene, in the range of from about 60 to about 80%. While the method mentioned above herein (the reaction of 4-dibenzo[b,d]thiophene boronic acid with bromobenzene) does not use the same precursors as the method of the present invention, its yield, based upon the dibenzo[b,d]thiophene precursor is roughly in the range of about 75% to about 90%. Given the fact the 4-dibenzo[b,d]thiophene boronic acid is generally significantly higher in price, on a molar basis, than the major synthetic precursors of the present invention (dichlorobenzene and bromobenzene), the process of the present invention is a far less costly alternative.

The following examples are presented for purposes of illustration, and are not intended to impose limitations on the scope of this invention.

EXAMPLE 1

Preparation of Phenyllithium—Lithium metal (35.4 g chunks, 5.10 mol) and ether (0.5 L) were charged to a three liter flask under an argon atmosphere. Bromobenzene (400 g, 2.55 mol) in ether (1.0 L) was added to the reactor from a dropping funnel over a period of about 2 hours. The ether refluxed during the addition. The reactor was stirred an additional hour after the reaction was complete.

Preparation of Meta-Terphenyl—The 1,3-dichlorobenzene (74.9 g, 0.51 mol) was added dropwise. The reaction was exothermic. The reaction was carried out in refluxing ether, and the reactor had a condenser set at −1° C. The reaction mixture was stirred for about 19 hours.

Preparation of Orthothiollithium metaterphenyl-(lithium terphenyl-2'-thiolate, lithium 2,6-diphenylthiolate.)—The reaction was cooled to about 1 C, and sulfur (64 g, 2.0 mol) was added in portions over 1 hour. The maximum temperature was 14.5 C. The reaction was stirred for 2 hours while warming to room temperature.

Preparation of Orthothiol metaterphenyl-(2,6-diphenyl thiophenol)—Concentrated hydrochloric acid (145 ml) in water (705 ml) was added dropwise.

Distillation to Remove Solvent, as Well as Thiophenol and Disulphide Byproducts—The acidic aqueous layer was drained from the reaction. A short path distillation head was attached to the reactor and the ether was distilled from the reactor. The reaction mass was filtered through celite under an inert atmosphere and the celite was washed with ether. The remaining ether was distilled from the reaction mass which was then put under vacuum to distill off volatiles until a pot temperature of 155° C. and a vacuum of 4.9 Torr were achieved. A Kugelrohr distillation was then carried out. Distillate collected in the ice-cooled bulb until a pot temperature of 134° C. and a vacuum of 0.5 Torr was reached. The purpose of the distillations was to remove most of the thiophenol and corresponding disulphide products.

Formation of Thiophene Ring to Give 4-phenyldibenzo[b,d]thiophene—The residue was a glass solid that was transferred with the aid of dichloromethane to a flask equipped with a stir bar. Sulfur (16.4 g, 0.511 mol) was charged to the flask. A short path distillation head was attached and the dichloromethane distilled off at atmospheric pressure. Over 3.5 h, the reaction mixture was heated from 66° C. to 226° C. The conversion was followed by GC and had achieved about 64% conversion to 4-phenyldibenzo[b,d]thiophene. The reaction mass achieved complete conversion after further heating for three hours at 234° C.

The crude product, weighing 157.4 g, was dissolved in toluene and agitated with 50 g silica gel. The silica gel was then filtered off. The crude product now weighed 140.5 g. The product was charged to a short path distillation head with a 1.5 inch built-in vigreaux column. The product distilled at approximately 180 C (0.7 Torr). Three fractions were collected with GC purities of 70.2% (fraction 1, 5.84 g), 92.5% (fraction 2, 98.5 g), and 56% (fraction 3, 16.1 g). The foregoing percentages are GC Area %, taken with an FID detector. Fraction 1, and to a lesser extent, fraction 2 contain solids that are most likely sulfur. Fractions 1 and 2 were dissolved in chloroform, cooled in a freezer, and then filtered to remove the solids. Yield based on fraction 2 and its GC purity is 67.6%, based upon moles of m-dichlorobenzene.

EXAMPLE 2

Preparation of Meta-Terphenyl—Commercial phenyllithium in dibutyl ether (660.3 g, 19.9%, 1.56 mol) was charged to a jacketed 2 L reactor equipped with a mechanical stirrer, addition funnel, and thermocouple. 1,3-Dichlorobenzene (46 g, 0.31 mol) was added dropwise. The temperature of the reactor reached 71° C., and a cooling unit with a set point of 25° C. was applied to the jacket of the reactor. The reactor was stirred about 20 h at ambient temperature, and was then cooled to 2° C.

Preparation of Orthothiollithium Metaterphenyl—Sulfur (39.6 g, 1.23 mol) was added in portions, maintaining the temperature below 10° C. The reaction was allowed to warm to ambient temperature over about two hours. Concentrated hydrochloric acid in water was added dropwise while maintaining the temperature at about 25° C. The acidic aqueous layer was drained from the reactor and a short path distillation head was attached to the reactor. Volatiles were distilled from the reactor until a pot temperature of 69.5° C. and a vacuum of 45.8 Torr were achieved. The reaction mass was transferred to a flask equipped with a 10 inch packed column and still head. Volatiles were distilled until a pot temperature of 108° C. and a vacuum of 3.4 Torr was achieved. The reaction mass was transferred to a Kugelrohr distillation apparatus and the volatiles were distilled until a pot temperature of 131° C. and a vacuum of 0.6 Torr was achieved. The weight of the residue was 84 g. The residue has the appearance of a dark, hard glass. Sulfur (10.2 g, 0.32 mol) was charged to the flask. The residue and sulfur were heated at 235° C. for 3 hours. After cooling, the residue was dissolved in chloroform and filtered through celite. The solvent was stripped off under reduced pressure using a rotovap, and the product was charged to a short path distillation head with a 1.5-inch built-in vigreaux column. The product distilled at approximately 180° C. (0.5 Torr). Three fractions were collected with GC purities of 81.3% (fraction 1, 15.3 g), 93.9% (fraction 2, 55.97 g), and 58.7% (fraction 3, 5.8 g). The foregoing percentages are GC Area %, taken with an FID detector. The weight and GC were taken on fraction one after it had been dissolved in chloroform, cooled, and filtered to remove some of its sulfur content. Yield based on fractions 1 and 2 and their GC purities is 79.9%, based upon moles of m-dichlorobenzene.

The yield number may be somewhat distorted due to some sulfur contamination, which would increase apparent yield. The impact on yield is not large.

EXAMPLE 3

Commercial phenyllithium in dibutyl ether (682.4 g, 20.6%, 1.67 mol) was charged to a jacketed 2 L reactor equipped with a mechanical stirrer and thermocouple. 1,3-dichlorobenzene (38.2 ml, 0.334 mol) was added by syringe pump over a period of two hours with the jacket of the reactor set at 25° C. The reaction was then stirred at 25° C. for about 14 hours. The reaction was cooled to less than 2° C. and sulfur (34.8 g) was added in portions maintaining the temperature below 10° C. After warming to ambient temperature, concentrated hydrochloric acid (117 ml) in water (550 ml) was added dropwise with the reactor jacket temperature set to 20° C. The acidic aqueous layer was drained off. The solvent and thiophenol were distilled off until a vacuum of 8 Torr and a pot temperature of 129° C. (overhead 42° C.) were achieved. Sulfur (8 g, 0.25 mol) was charged to the residue, and the mixture was heated under nitrogen at 235° C. for 6 hours. Additional sulfur (1 g, 0.031 mol) was charged and the sample was heated an additional three hours. The product was charged to a short path distillation head with a 1.5 inch built-in vigreaux column. The main fraction distilled at 181-185° C. (0.6 Torr, pot 215° C.) and weighed 70.1 g (GC purity 93.34%). The foregoing percentages are GC Area %, taken with an FID detector. Yield is 75%, based upon moles of m-dichlorobenzene.

EXAMPLE 4

Anhydrous ether (500 ml) and lithium wire (28.7 g, 4.13 mol) was charged to a jacketed 3 L flask equipped with a bottom outlet, condenser and addition funnel under an atmosphere of argon. Bromobenzene (324.6 g, 2.07 mol) in anhydrous ether (1000 ml) was added dropwise to the reactor over a period of 3 hours. The reaction was exothermic and the ether refluxed during the addition. Thirty minutes after the end of the addition of bromobenzene, m-dichlorobenzene (60.7 g, 0.413 mol) was charged dropwise to the reactor from the addition funnel. The addition was exothermic and the ether refluxed. After stirring for about 16 hours at ambient temperature, sulfur (52.5 g, 1.64 mol) was added in portions over an hour. The reaction was again exothermic. Concentrated hydrochloric acid (118 ml) in water (765 ml) was added dropwise. The acidic aqueous layer was drained from the reactor. Most of the solvent was distilled off, and the reaction mass was then filtered under an inert atmosphere and transferred to a Kugelrohr distillation pot. Side-products diphenyl disulfide and thiophenol were distilled from the reaction mass. The final temperature of the pot was 134° C. at 0.38 Torr. The reaction mass was dissolved in chlorobenzene (100 ml) under an inert atmosphere. Isohexane (100 ml) and triethylamine (0.4 ml, 0.003 mol) were charged to the flask. The reaction mass was cooled in an ice bath and sulfuryl chloride (27.2 ml, 0.336 mol) was charged to the cooled reaction mass from a dropping funnel. After stirring 16 h at ambient temperature, the excess sulfuryl chloride and a portion of the solvent were distilled off. Final temperature of the pot was 23° C. at 8.9 Torr. The reaction mass was dissolved in more chlorobenzene (200 mil) and cooled to −9° C. Aluminum chloride (0.5 g, 0.0037 mol) was charged to the reactor. The reaction warmed to room temperature over 16 h and was then poured into aqueous sodium bicarbonate. It was extracted with dichloromethane and the organic layer was dried over magnesium sulfate. The solvents were distilled off under reduced pressure. The crude phenyl dibenzothiophene was distilled through a short path at 184° C. to 210° C. (0.95 Torr). The highest purity fraction was 80%, (based upon gas chromatographic analysis) and the overall yield was only about 35%, based upon moles of m-dichlorobenzene.

However, examination of the Kugelrohr distillate by GC indicated that a significant amount of diphenylphenol distilled over with the diphenyl sulfide and was lost to the process.

Components referred to by chemical name or formula anywhere in the specification or claims hereof, whether referred to in the singular or plural, are identified as they exist prior to coming into contact with another substance referred to by chemical name or chemical type (e.g., another component, a solvent, or etc.). It matters not what chemical changes, transformations and/or reactions, if any, take place in the resulting mixture or solution as such changes, transformations, and/or reactions are the natural result of bringing the specified components together under the conditions called for pursuant to this disclosure. Thus the components are identified as ingredients to be brought together in connection with performing a desired operation or in forming a desired composition. Also, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. The fact that a substance, component or ingredient may have lost its original identity through a chemical reaction or transformation during the course of contacting, blending or mixing operations, if conducted in accordance with this disclosure and with ordinary skill of a chemist, is thus of no practical concern.

The invention may comprise, consist, or consist essentially of the materials and/or procedures recited herein.

As used herein, the term "about" modifying the quantity of an ingredient in the compositions of the invention or employed in the methods of the invention refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term about also encompasses amounts that differ due to different equilibrium conditions for a composition resulting from a particular initial mixture. Whether or not modified by the term "about", the claims include equivalents to the quantities.

Except as may be expressly otherwise indicated, the article "a" or "an" if and as used herein is not intended to limit, and should not be construed as limiting, the description or a claim to a single element to which the article refers. Rather, the article "a" or "an" if and as used herein is intended to cover one or more such elements, unless the text expressly indicates otherwise.

Each and every patent or other publication or published document referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove.

That which is claimed is:

1. A method for the preparation of a 4-phenyldibenzo[b,d]thiophene, the method comprising the following steps:
   a) reacting a dihalobenzene with a phenyllithium to give a terphenyllithium:

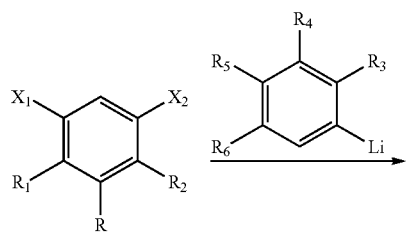

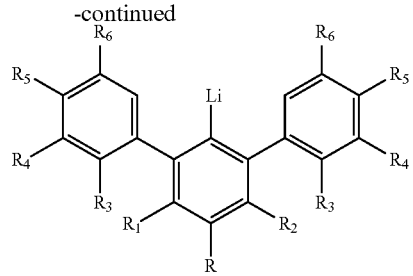

b) reacting the terphenyllithium with sulfur to give a thiollithium:

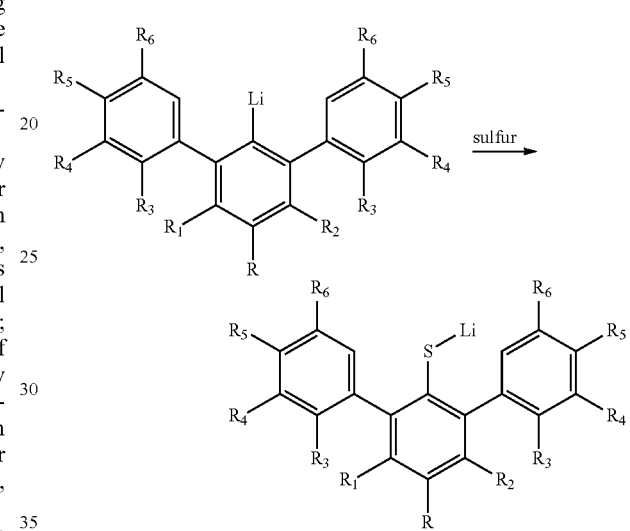

c) treating the thiollithium with an acid to form a thiol; and
   d) reacting the thiol with an oxidizer to form the 4-phenyldibenzo[b,d]thiophene:

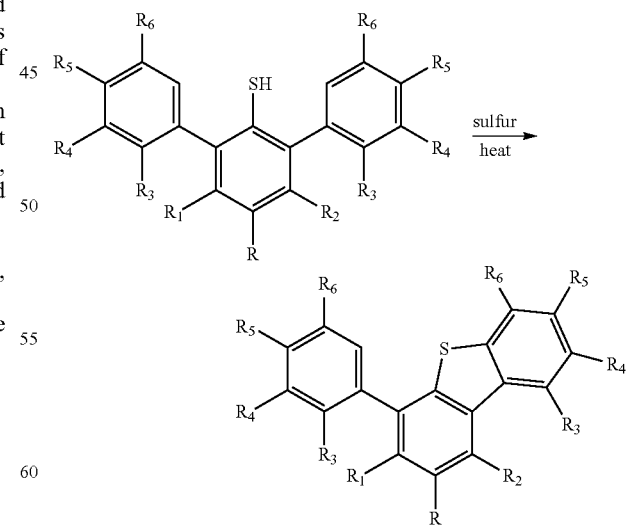

wherein R, $R_1$, $R_2$, $R_3$, $R_4$, $R_5$, and $R_6$ are each independently selected from the group consisting of hydrogen, phenyl, an alkyl substituent ($-C_n$) and an ether substituent ($-C_{m1}-O-C_{m2}$), where n, m1 and m2 are each an integer, with each of n and (m1+m2+1) being in the range of 0 to 16; and wherein $X_1$ and $X_2$ are each independently selected from the group consisting of chlorine, iodine and bromine.

2. A method as in claim 1, wherein each of n and (m1+m2+1) is in the range of 0 to 6.

3. A method as in claim 1 wherein $X_1$ and $X_2$ are each chlorine; $X_1$ is chlorine and $X_2$ is iodine; $X_1$ is chlorine and $X_2$ is bromine; or $X_1$ and $X_2$ are each bromine.

4. A method as in claim 3 wherein R, $R_1$ or $R_2$ are each, independently, an alkyl group.

5. A method as in claim 4 wherein each of R, $R_1$, $R_2$, $R_3$, $R_4$, $R_5$ and $R_6$ is hydrogen.

6. A method as in claim 1 wherein the oxidizer in step d) comprises sulfur.

7. A method as in claim 2 wherein the oxidizer in step d) comprises sulfur.

8. A method as claim 3 wherein the oxidizer in step d) comprises sulfur.

9. A method as claim 4 wherein the oxidizer in step d) comprises sulfur.

10. A method as in claim 5 wherein the oxidizer in step d) comprises sulfur.

\* \* \* \* \*